United States Patent [19]

Chretien et al.

[11] Patent Number: 5,468,729
[45] Date of Patent: Nov. 21, 1995

[54] METHOD FOR TREATMENT OF AUTOIMMUNE HEPATITIS

[75] Inventors: Paul B. Chretien, Rockville, Md.; Milton G. Mutchnick, West Bloomfield, Mich.

[73] Assignees: Alpha 1 Biomedicals, Bethesda, Md.; The Board of Governers of Wayne State University, Detroit, Mich.

[21] Appl. No.: 141,013

[22] Filed: Oct. 26, 1993

[51] Int. Cl.$^6$ .......................... A61K 38/04; A61K 31/56; C07K 14/475; C07J 51/00
[52] U.S. Cl. ...................... 514/12; 514/2; 514/885; 514/179; 530/324; 530/399; 552/576; 435/240.1
[58] Field of Search .................................. 514/2, 885, 12, 514/179; 530/324, 399; 552/576; 435/240.1

[56] References Cited

U.S. PATENT DOCUMENTS 4,444,757  4/1984  Stausser .................................. 424/177

FOREIGN PATENT DOCUMENTS 9305806  4/1993  WIPO .

OTHER PUBLICATIONS

Eichberg et al., "Effect of Thymosin Immunostimulation With and Without Corticosteroid Immunosuppression on Chimpanzee Hepatitis B Carriers", *Journal of Medical Virology*, 21:1, pp. 25–37, Jan. 1987.
Kurbanov, T. G., et al., "Efficacy of the Use of Tymalin in Children With Diabetes Mellitus", *Probl–Endokrinol* (Mosk) 1989; 35(6):7–9.

O'Brien, C. J., et al., "In Vitro Effect of TP-1 (A Calf Thymic Extract) on Suppressor T-Cell Function of Patients with Autoimmune Chronic Active Hepatitis", *Int. J. Immnopharmac.*, vol. 10, No. 6, pp. 651–656, 1988.
Marshall, G. D., Jr. et al., "In Vivo Generation of Surppressor T Cells by Thymosin in Congenitally Athymic Nude Mice", *The Journal of Immunology*, vol. 126, No. 2, pp. 741–744, Feb. 1981.
Low, T. L. K., et al., "The Chemistry and Biology of Thymosin", *The Journal of Biological Chemistry*, vol. 254, No. 3, Feb. 10, pp. 981–986, 1979.
Hegarty, J. E., et al., "Controlled Trial of a Thymic Hormone Extract (Thymostimulin) in 'Autoimmune' Chronic Active Hepatitis", *Gut*, 1984, 25, 279–283.
Pernice, W., et al., "Steroid Economising Effects of a Calf Thymus Extract in Three Patients with Juvenile Chronic Arthritis", *Klinische Wochen–Schrift*, (1983), 61:429–431.
Jacobs, R. P. et al., "Treatment of Rheumatoid Arthritis With Thymosin: Preliminary Immunologic Studies", *Thymic Factor Therapy*, Byrom, N. A. and Hobbs, J. R. eds., New York, Raven Press, pp. 267–276 (1984).
Goldstein et al., "Potential Role of Thymosin in The Treatment of Autoimmune Diseases", *Ann. N.Y. Acad. Sci.*, 377:486–495 (1981).
Laskin et al., Am. J. of Med., vol. 89, 129–133, 1990.
Antiviral Agents Bulletin, vol. 4, No. 10, Oct. 1991.
Lavastida et al., Thymus, vol. 2, 287–296, 1981.

*Primary Examiner*—David L. Lacey
*Assistant Examiner*—Ron Schwadron
*Attorney, Agent, or Firm*—Rothwell, Figg, Ernst & Kurz

[57] ABSTRACT

A method and composition for treating autoimmune hepatitis in a patient utilizes an immunomodulatory amount of $T\alpha_1$ and an anti-inflammatory amount of a corticosteroid.

14 Claims, No Drawings

METHOD FOR TREATMENT OF AUTOIMMUNE HEPATITIS

BACKGROUND OF THE INVENTION

1. Field of the Invention

The present invention relates to a method and composition for treating autoimmune hepatitis in mammals.

2. Description of Background Art

The term "autoimmune disorder" is an umbrella-like term which is used to refer to a large group of unrelated illnesses with unknown causes, but associated with abnormalities in immunoregulation.

Hepatitis is an inflammatory process in the liver which can be caused by a variety of aetiologies, including viruses and drugs.

When a patient is suffering from a chronic hepatitis, but the cause of the disease is not known (i.e., following exclusion of other causes), and is associated with abnormalities in immunoregulation, the patient is said to have "autoimmune hepatitis". Untreated, autoimmune hepatitis is progressive, and can result in liver failure and death.

One current treatment for autoimmune hepatitis requires prolonged administration of corticosteroids such as prednisone and prednisolone. While corticosteroid therapy has been shown to extend life, improve biochemical abnormalities and enhance quality of life in many patients, the beneficial effects of corticosteroids are offset by the often serious complications and side effects associated with the prolonged treatment therewith.

While there have been several proposals for treating autoimmune hepatitis with extracts of calf thymus (e.g., Hegarty et al., Gut 25:279–283 (1984), and O'Brien et al., Int. J. Immunopharmac. 10:651–658 (1988)), none have heretofore been shown to be successful.

There remains a need in the art for new and improved methods and compositions for treating autoimmune hepatitis.

SUMMARY OF THE INVENTION

In accordance with the present invention, a method of treating autoimmune hepatitis in a patient comprises administering to a patient in need of such treatment a drug regimen comprising an immunomodulatory amount of Thymosin $\alpha_1$ and an anti-inflammatory amount of a corticosteroid.

The invention further includes a pharmaceutical composition comprising separate pharmaceutical dosage units of an immunomodulatory amount of Thymosin $\alpha_1$ and an anti-inflammatory amount of a corticosteroid.

DESCRIPTION OF THE PREFERRED EMBODIMENTS

Autoimmune hepatitis is referred to as such because it is a chronic hepatitis of unknown aetiology. Other causes of autoimmune hepatitis must be excluded. Autoimmune hepatitis can further be classified as follows.

Type 1, or "classic" autoimmune hepatitis, is characterized in patients by the presence of antinuclear antibodies (ANA) in approximately 70% of such patients, the presence of anti-smooth muscle (anti-actin) antibodies (SMA) in more than 30% of such patients, and sensitivity to corticosteroids.

Type 2 autoimmune hepatitis is characterized by the presence of anti-liver-kidney-microsomal antibodies (ANTI-LKM-1), absence of ANA and SMA, and sensitivity to corticosteroids.

Type 3 autoimmune hepatitis patients are characterized by the presence by liver-pancreas antigen antibody (ANTI-LP) or anti-soluble liver antigen antibodies (ANTI-SLA), absence of ANA and ANTI-LKM-1, presence of SMA in 30% of such patients, and sensitivity to corticosteroids.

Type 4 autoimmune hepatitis patients are characterized as cryptogenic (tentative), and are characterized by the absence of ANA, SMA, ANTI-LKM-1, ANTI-SLA and ANTI-LP, and sensitivity to corticosteroids.

It has surprisingly been discovered that Thymosin $\alpha_1$ and corticosteroids appear to act synergistically in the treatment of autoimmune hepatitis.

As noted above, a method of treating autoimmune hepatitis in a patient in accordance with the present invention, comprises administering to a patient in need of such treatment a drug regimen comprising an immunomodulatory amount of Thymosin $\alpha_1$ and an anti-inflammatory amount of a corticosteroid. Suitable corticosteroids for use in accordance with the present invention include, but are not limited to, prednisone and prednisolone.

Anti-inflammatory amounts of a corticosteroid are included within the dosage range of about 1–100 mg. Preferably, the amount of corticosteroid administered is sufficient to reduce serum transaminase levels of the patient, decrease necroinflammatory activity in the liver and inhibit progression of liver cirrhosis.

The terms "Thymosin $\alpha_1$ and "T$\alpha_1$" as used herein encompasses not only native (i.e., naturally occurring) T$\alpha_1$ but also synthetic T$\alpha_1$ and recombinant T$\alpha_1$ having the amino acid sequence of native T$\alpha_1$, amino acid sequences substantially similar thereto, or an abbreviated sequence from thereof, and their biologically active analogs (including muteins) having substituted, deleted, elongated, replaced, or otherwise modified sequences which possess bioactivity substantially similar to that of T$\alpha_1$.

Immunomodulatory amounts of Thymosin $\alpha_1$ are included within the dosage range of 0.4–4 mg. Such amounts can be sufficient to stimulate T-lymphocytes and CD4 cells in autoimmune hepatitis patients.

Without being bound to any particular theory, disturbances in immunoregulation may see expression in the control of autoreactivity in autoimmune hepatitis. The perturbation may reside in subsets of T-cells or reflect the influence of cytokine mediators on antigen-presenting cells, autoreactive T-cells or, on cell surfaces of hepatocytes.

The course of the autoimmune hepatitis and its response to treatment may be followed by clinical examination and laboratory findings. Elevated serum transaminases, including serum alanine aminotransferase (ALT) and aspartate aminotransferase (AST) occur in uncontrolled autoimmune hepatitis. A treatment response can be defined as reduction of serum transaminase levels to about two times the upper limit of normal serum transaminase levels. Baseline values for normal serum transaminase levels may very according to the assay used, but typically, high normal values are within the range of about 35–65 IU/L for ALT or AST. A complete response to treatment can be defined as normalization of these serum enzymes, particularly ALT. Accordingly, progress of treatment can conveniently be followed by measuring serum transaminases levels, for example, on a sequential multiple analyzer.

A preferred embodiment in accordance with the present invention involves administration of a regimen of doses of anti-inflammatory amounts of a corticosteroid, without administration of $T\alpha_1$, so as to reduce transaminase levels of the patient to a target level of less than about two times the upper limit of normal serum transaminase levels, or to normal or near normal levels if possible. After reduction of the patient's transaminase levels to the target levels, the patient's maintenance dose of corticosteroid can be determined. Then, administration of a dose regimen of an immunomodulatory amount of $T\alpha_1$ can be commenced, while continuing corticosteroid administration. During subsequent co-administration of the corticosteroid and $T\alpha_1$, the patient's maintenance dose of corticosteroid may be reduced, while maintaining the serum transaminase levels at or below the target levels.

In particularly preferred embodiments, Thymosin $\alpha_1$ is administered by subcutaneous injection twice weekly at a dose within the range of about 1–4 mg (e.g., about 1.6 mg), and the corticosteroid is administered orally once daily, or on an alternating day regimen, at a dose within the range of about 2–60 mg. However, it is to be understood that separate pharmaceutical dosage units containing Thymosin $\alpha_1$ and the corticosteroid, respectively, may be formulated in any suitable manner for administration by any suitable route. Suitable routes of administration may include, but are not limited to, oral, parenteral (including subcutaneous, intramuscular, intravenous and intradermal) and transdermal. Particularly preferred embodiments utilize parenteral and/or oral administration.

In preferred embodiments, $T\alpha_1$ and the corticosteroid are administered as separate pharmaceutical dosage units. The separate dosage units of the present invention include one or more pharmaceutically acceptable carriers and optionally other therapeutic ingredients. The carrier(s) are "acceptable" in the sense of being compatible with the other ingredients of the dosage unit formulation and not deleterious to the recipient thereof.

The separate dosage unit formulations may be prepared by any suitable pharmaceutical methods.

Such methods may include the step of separately bringing into association the respective active ingredient ($T\alpha_1$ or the corticosteroid) with its carrier, which may comprise one or more ingredients. In general, the formulations are prepared by uniformly and intimately bringing into association the respective active ingredient with liquid carriers or finely divided solid carriers or both. Solid dosage unit formulations also may include the step of shaping the product.

Formulations of the present invention suitable for oral administration may be presented as discrete units such as capsules, cachets or tablets, containing a predetermined amount of the particular active ingredient; as a powder or granules; as a solution or a suspension in an aqueous liquid or a non-aqueous liquid; or as an oil-in-water liquid emulsion or a water-in-oil liquid emulsion, etc.

A tablet may be made by compression or molding, optionally with one or more accessory ingredients. Compressed tablets may be prepared by compressing, in a suitable machine, free-flowing powder or granules, optionally mixed with a binder, lubricant, inert diluent, preservative, surface-active or dispersing agent. Molded tablets may be made by molding, in a suitable machine, a mixture of the powdered compound moistened with an inert liquid diluent. Tablets may optionally be coated or scored and may be formulated so as to provide slow or controlled release of the active ingredient therein.

Formulations suitable for parenteral administration include aqueous and non-aqueous sterile injection solutions which may optionally contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) condition requiring only the addition of the sterile liquid carrier, for example water for injection, immediately prior to use. Extemporaneous injection solutions and suspensions may be prepared from sterile powders, granules and tablets of the kind previously described.

Suitable dosage units of $T\alpha_1$ and the corticosteroid can be administered to the patient daily, one or more times per day, e.g., two or three times per day, and doses can be administered one or more days per week, e.g., two, three, four, five, six or seven days per week.

The invention is further illustrated by the following examples, which are not intended to be limiting. The examples involve four patients (two women and two men) with Type 1 autoimmune hepatitis. Three of the patients were previously receiving prednisone, and one patient was newly diagnosed and untreated. In each case, $T\alpha_1$ was administered at a dosage level of 1.6 mg by subcutaneous injection, twice weekly.

EXAMPLE 1

Patient was a 52 year old white female diagnosed with chronic autoimmune hepatitis at age 45. Patient presented with elevated transaminases, fatigue and lower extremity edema. At that time her transaminases were 6 to 10 times the upper limit of normal. A biopsy showed chronic active cirrhosis and serologies were positive for ANA and SMA.

Patient was started on 40 mg of prednisone daily. A slow taper was undertaken. Patient's transaminases remained near normal at a dose of 12.5 mg per day. However, with subsequent attempts to lower the prednisone dose further, patient's transaminases would flare. At this dose she had some problems with fluid retention and dyspepsia.

She was offered 1.6 mg Thymosin $\alpha_1$ injections twice weekly. She agreed to this trial and injections were then started. The prednisone was eventually decreased to 2.5 mg every other day. At this low dose, she did have a transient flare in her transaminases and the prednisone was temporarily increased back to 20. Subsequently, on a continued does of 5 mg a day, patient did well. Her transaminases remained near normal and she experienced no further problems with fluid retention. She was able to discontinue her diuretics.

After maintaining the transaminases with twice weekly thymosin injections and prednisone at 5 mg a day, we elected to discontinue thymosin and observe the results. She experienced an increase in her transaminases and the thymosin was thus subsequently restarted, along with prednisone at 10 mg daily, with normalization once again of her transaminases.

The patient has continued on thymosin injections now for 3 years with no significant or persistent side effects. Thymosin appears to have some steroid sparing effect as the prednisone dose is now stable at 7.5 mg daily.

EXAMPLE 2

Patient was an 18 year old white male with a diagnosis of chronic autoimmune hepatitis and cirrhosis. This diagnosis was made by liver biopsy and compatible serology (ANA of 1 to 10,000 and ASMA of 1 to 2560). His problems began 18 months prior to the diagnosis with his initial episode of jaundice. He was otherwise asymptomatic at that time, although his liver enzymes were markedly abnormal.

He had spontaneous remission of his jaundice and did well until approximately 12 months later when he had a recurrent episode. At that time he had associate symptoms of acholic stools and dark urine. He continued to do well until he presented with epistaxis and hematochezia. Because of adenopathy, splenomegaly, and hematologic abnormalities a diagnosis of lymphoma was entertained initially. However, further evaluation including exploratory laparotomy with splenectomy and liver biopsy, as well as several blood tests, finally confirmed the diagnosis of autoimmune hepatitis with cirrhosis.

Because of the patient's splenectomy, he was at an increased risk for infection. This problem could potentially be exacerbated with the use of prednisone. Therefore, the patient was offered the option of $T\alpha_1$ treatment alone. He elected to pursue this option and was started on 1.6 mg $T\alpha_1$ injections twice weekly. At the time of drug initiation the ALT was 247, AST 382. These injections continued for approximately 5 weeks. However, shortly after one month after commencing treatment, it was apparent that his transaminases were not responding, the ALT was 396 and AST 695. Therefore, $T\alpha_1$ was discontinued and the patient was started on prednisone. He responded to the prednisone therapy with a substantial decrease and eventual normalization in his transaminases.

EXAMPLE 3

Patient was a 46 year old white male with a diagnosis of chronic autoimmune hepatitis. His presenting symptoms were fatigue, myalgia and jaundice. A liver biopsy showing chronic active hepatitis with early cirrhosis and positive ANA and anti-smooth muscle antibodies confirmed the diagnosis.

His initial therapy consisted of imuran 50 mg/day and prednisone at 30 mg/day. This therapy was instituted at the time of diagnosis when his transaminases were approximately 10 times the upper limit of normal. The enzymes declined with this therapy, however, the patient had problems with irritability and weight gain. Initial attempts at tapering the prednisone were unsuccessful. At a prednisone level of 20 mg/day his AST was elevated to 421 and his ALT remained high at 503. An increase in the prednisone to 40 mg again resulted in near normalization of the transaminases and it was at this point that the patient's imuran was discontinued. However, the enzymes again became elevated and it was necessary to dose the patient with 60 mg of prednisone each day. This maneuver resulted in laboratory improvement but the patient unfortunately developed steroid induced diabetes.

Because of the high doses of prednisone required to control the patient's disease process and the side effects associated with these doses, the patient was offered $T\alpha_1$. The response to twice weekly 1.6 mg $T\alpha_1$ injections was favorable with a definite steroid sparing effect observed. Within 1 week the ALT decreased from 212 to 140 and the AST from 124 to 70. We were able to decrease the prednisone to 7.5 mg every day while maintaining steady transaminase values. Unfortunately we were not able to decrease transaminases to less then 2 times the upper limit of normal. After approximately 6 weeks on prednisone at 7.5 mg/day we therefore elected to increase the patient's prednisone back to 40 mg/day. This resulted in prompt improvement of the transaminases with declining values to near normal range. After patient had maintained these normal values for approximately 8 weeks, we elected to arbitrarily stop the $T\alpha_1$ injections. Over the next 8 weeks the transaminase values again began to rise, however, with reinstitution of thymosin therapy this time we were not able to recognize a decline in the transaminase values and therefore the $T\alpha_1$ injections were discontinued. Patient was started on imuran therapy in addition to his prednisone at 60 mg/day and after several weeks on imuran we have seen near normalization of his transaminases once again.

Aside form the improvement in 'laboratory parameters the patient also experience clinical benefit from the $T\alpha_1$. While taking the injections, his insulin requirements decreased and his energy level had increased and his irritability had subsided.

EXAMPLE 4

Patient was a 39 year old black female with a diagnosis of chronic autoimmune hepatitis. This diagnosis was made on the basis ASMA and ANA positivity as well as a liver biopsy showing active cirrhosis. The patient's initial presentation was that of anemia and coagulopathy.

She was stared on prednisone therapy with improvement in transaminase values. However she developed a upper GI bleed secondary to duodenal ulcer and at doses of prednisone, 40 mg/day, had significant problems with irritability, restlessness and mood swings. These side effects necessitated a decrease in her prednisone dose. However, at doses less than 40 mg/day, her disease activity was not controlled.

Because of the side effects of prednisone in this patient, $T\alpha_1$ therapy was offered to her as an alternative to imuran. She therefore was started on 1.6 mg $T\alpha_1$ injections twice weekly and on prednisone at a dose of 20 mg/day. Within 2 weeks, the ALT had decreased from 230 to 126 and the AST from 257 to 138. Over the next 4 months a slow prednisone taper to 7.5 mg/day was successful in that her transaminases remained steady at about 3 times the upper limit of normal. After approximately 1 month of prednisone at 7.5 mg/day followed by 5.0 mg/day for 1 week, we saw an increase in her transaminase levels and therefore elected to increase her prednisone to 30 mg/day. This resulted in prompt decrease in her transaminases to less than 2 time the upper limit of normal. Upon maintaining this normalization for 1 month, we arbitrarily elected to stop $T\alpha_1$ injections, and increase prednisone to 40 mg/day, and observe possible effect. We did notice a gradual increase in the patient's transaminase values. Upon reinstituting $T\alpha_1$ therapy we failed to observe the previously identified immunosparing effect. The patient's transaminases had elevated to more than 3 time the upper limit of normal and we therefore discontinued the $T\alpha_1$ and instituted imuran therapy. While on $T\alpha_1$ therapy the patient did note some clinical improvement, with lessening of her lower extremity edema, irritability and fatigue.

Examples 1, 3 and 4 show successful use of $T\alpha_1$ combined with prednisone in treating autoimmune hepatitis and improving transaminases. These results also show the corticosteroid sparing effect of $T\alpha_1$.

Example 1 further illustrates a preferred embodiment of the invention, wherein $T\alpha_1$ administration is commenced after transaminases have been normalized with corticosteroids and the patient's maintenance dose of corticosteroids has been determined.

In Example 2, Tα₁ was not effective as sole therapy for autoimmune hepatitis.

The results indicated a synergistic activity of combined treatment with Tα₁ and corticosteroid, in which the disease can be treated at reduced corticosteroid levels.

What is claimed is:

1. A method of treating autoimmune hepatitis in a patient, comprising administering to a patient in need of such treatment a drug regimen comprising an immunomodulatory amount of Thymosin $\alpha_1$ (T$\alpha_1$) and an anti-inflammatory amount of a corticosteroid.

2. The method of claim 1 wherein said T$\alpha_1$ is administered in a dosage amount within the range of about 0.4–4 mg.

3. The method of claim 1 wherein said T$\alpha_1$ is administered in a dosage amount within the range of about 1–4 mg.

4. The method of claim 1 wherein said T$\alpha_1$ is administered in a dosage amount of about 1.6 mg.

5. The method of claim 1 wherein said T$\alpha_1$ is administered to said patient two times weekly by subcutaneous injection.

6. The method of claim 1 wherein said corticosteroid is administered in a dosage amount within the range of about 1–100 mg.

7. The method of claim 1 wherein said corticosteroid is administered in a dosage amount within the range of about 2–60 mg.

8. The method of claim 1 wherein said corticosteroid is prednisone, and said prednisone is administered once daily.

9. The method of claim 1 wherein said corticosteroid is prednisone, and said prednisone is administered on an alternating day regimen.

10. The method of claim 1 wherein said corticosteroid is administered to said patient in a liver necroinflammatory-inhibiting amount.

11. The method of claim 1 wherein said corticosteroid is administered to said patient in a liver cirrhosis progression-inhibiting amount.

12. The method of claim 1 wherein said drug regimen is administered to said patient so as to maintain ALT levels of said patient at less than about two times an upper limit of normal for said ALT levels, wherein said upper limit of normal for ALT levels is 35–65 IU/L.

13. The method of claim 12 wherein, prior to administration of said drug regimen including both said T$\alpha_1$ and said corticosteroid, a transaminase-reducing amount of said corticosteroid is administered to said patient without administering T$\alpha_1$, so as to reduce serum ALT levels of the patient at less than about two times an upper limit of normal for said ALT levels wherein said upper limit of normal for ALT levels is 35–65 IU/L.

14. The method of claim 13 wherein, during administration to said patient of the drug regimen comprising T$\alpha_1$ and said corticosteroid, further including the step of reducing dosage of said corticosteroid administered to said patient, while administering both T$\alpha_1$ and said corticosteroid to said patient, and while maintaining said ALT level of said patient at less than about two times an upper limit of normal for said ALT levels, wherein said upper limit of normal for ALT levels is 35–65 IU/L.

* * * * *

UNITED STATES PATENT AND TRADEMARK OFFICE
CERTIFICATE OF CORRECTION

PATENT NO. : 5,468,729
DATED : November 21, 1995
INVENTOR(S) : Paul B. Chretien et al.

It is certified that error appears in the above-indentified patent and that said Letters Patent is hereby corrected as shown below:

Column 2, line 58, "very" should be -- vary --; Col. 4, line 48, "does" should be -- dose --; Col. 6, line 14, delete the apostrophe before "laboratory";
In the Claims: Col. 8, line 19 (claim 13), after "levels" insert a comma.

Signed and Sealed this

Ninth Day of July, 1996

Attest:

BRUCE LEHMAN

Attesting Officer  Commissioner of Patents and Trademarks